United States Patent
Bhat (12)
(10) Patent No.: US 6,645,135 B1
(45) Date of Patent: Nov. 11, 2003

(54) INTRAVASCULAR CATHETER DEVICE AND METHOD FOR SIMULTANEOUS LOCAL DELIVERY OF RADIATION AND A THERAPEUTIC SUBSTANCE

(75) Inventor: Vinayak D. Bhat, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 201 days.

(21) Appl. No.: 09/823,426

(22) Filed: Mar. 30, 2001

(51) Int. Cl.[7] ................................................. A61N 5/00
(52) U.S. Cl. ............................ 600/3; 600/7; 604/96.01
(58) Field of Search .................. 600/3, 7, 8; 604/19–22, 604/95–103; 606/194

(56) References Cited

U.S. PATENT DOCUMENTS

| 5,458,568 | A | * | 10/1995 | Racchini et al. ............... 604/19 |
| 5,628,730 | A | * | 5/1997 | Shapland et al. .............. 604/21 |
| 5,643,171 | A | * | 7/1997 | Bradshaw et al. .............. 600/1 |
| 5,797,948 | A | * | 8/1998 | Dunham ....................... 606/194 |
| 5,910,101 | A | | 6/1999 | Andrews et al. ................ 600/3 |
| 6,511,503 | B1 | * | 1/2003 | Burkett et al. .............. 623/1.11 |

* cited by examiner

*Primary Examiner*—Thor Campbell
(74) *Attorney, Agent, or Firm*—Squire, Sanders & Dempsey, L.L.P.

(57) ABSTRACT

Methods and devices for providing intravascular local radiation therapy and simultaneous local delivery of a solution of a therapeutic substance are disclosed. The therapeutic substance may be an antiplatelet substance, an antithrombotic substance, a thrombolytic substance, or a mixture thereof, among other possibilities. An exemplary balloon catheter assembly for delivery of the simultaneous radiation and therapeutic substance treatments includes an elongate body with lumen for delivering the solution of the therapeutic substance to a permeable inflation region at a distal end of the body, and a centerable delivery lumen for transporting a radiation source to the treatment site.

10 Claims, 6 Drawing Sheets

INTRAVASCULAR CATHETER DEVICE AND METHOD FOR SIMULTANEOUS LOCAL DELIVERY OF RADIATION AND A THERAPEUTIC SUBSTANCE

BACKGROUND OF THE INVENTION

1. Field of the Invention

The present invention involves medical devices that are capable of providing intravascular radiation therapy.

2. Description of the Related Art

Percutaneous transluminal coronary angioplasty (PTCA) is a medical procedure used to open arteries that have been partially closed ("stenosed") by the buildup of atherosclerotic plaque or other materials, and accordingly pass a reduced amount of blood. In a typical PTCA procedure, a guiding catheter having a preformed distal tip is percutaneously introduced into the cardiovascular system of a patient through the brachial or femoral arteries. The guiding catheter is advanced therein until the distal tip is in the ostium of the desired coronary artery. A guide wire and dilation catheter having an inflatable balloon on the distal end thereof are introduced through the guiding catheter with the guide wire slidably disposed within an inner lumen of the dilation catheter. The guide wire is first advanced out of the distal end of the guiding catheter and is then maneuvered into the patient's coronary vasculature containing the lesion to be dilated, and is then advanced beyond the lesion. Thereafter, the dilation catheter is advanced over the guide wire until the dilation balloon is located across the lesion. Once in position across the lesion, the balloon is inflated to a predetermined size to radially compress against the atherosclerotic plaque of the lesion for remodeling the vessel. The balloon is then deflated so that the dilation catheter can be removed and blood flow resumed through the dilated artery.

After an angioplasty procedure, restenosis at or near the site of the original stenosis in the artery occasionally occurs. The smooth muscle cells of the artery may proliferate at the site of angioplasty treatment. Restenosis may result in a reformation of the lesion and a narrowing of the artery at the site.

Various devices and methods for the prevention of restenosis have been developed, including the use of an expandable stent on the distal end of the catheter designed for long-term implantation in the body lumen. Other devices and methods for the prevention of restenosis after angioplasty or another arterial intervention procedure employ a radiation source delivered through a balloon. The radiation operates to destroy the proliferating cells, thereby preventing development of restenosis. A medical device and method for such a radiation therapy is described in U.S. Pat. No. 5,910,101, which is incorporated herein by reference in its entirety.

An undesirable effect of radiation therapy, however, is that endothelial cells of the vessel at the treatment site are destroyed. Moreover, re-endothelialization, which is the re-growth of endothelial cells from neighboring areas over the area provided with radiation therapy, does not readily occur. Recent research has shown that endothelial cells perform various functions that help to maintain the health of a blood vessel, including producing nitric oxide, and regulating the concentration of pro-thrombotic and anti-thrombotic materials in the bloodstream. Absent sufficient re-endothelialization, conditions such as acute thrombosis, platelet aggregation at the site of radiation, and acute closure of the vessel, can occur. As a result of these conditions, the time required for the vessel to heal is increased.

To address such conditions, patients who undergo PTCA and radiation therapy receive an antiplatelet drug, such as heparin, by systemic administration for a period of two to three months after the PTCA procedure. However, there are drawbacks to such systemic therapy. For example, patients sometimes fail to comply with a prescribed systemic drug therapy regime for such a long period of time. Moreover, since the heparin or other antiplatelet drug is administered systemically, rather than locally, high dosages must be provided to yield a therapeutic effect. Such high dosages can result in undesirable complications in the patient, such as internal bleeding, and aneurysms.

Thus, there is a need for an improved method of providing intravascular radiation therapy after a PTCA procedure or other interventional procedure that reduces the risk of delayed reendothelialization, combats restenosis, advances the goals of the PCTA or other interventional procedure, and/or otherwise promotes the health of the vessel and surrounding tissue.

SUMMARY

The present invention provides methods and structures for locally delivering a simultaneous radiation treatment and drug treatment to an intravascular treatment site. By providing both types of treatments simultaneously in one surgical procedure, common problems that can arise after, for example, PCTA procedures, such as restinosis and/or delayed reendotheliallization, can be addressed in a preventative manner.

In accordance with one embodiment of the present invention, a method for treating a vascular lumen and surrounding tissue is provided. The method includes locally delivering a therapeutic substance to a treatment site in a vascular lumen contemporaneous with locally delivering a radiation treatment to the treatment site. For example, the delivery of the therapeutic substance may be simultaneous with the radiation treatment. The therapeutic substance may be an antiplatelet substance, an antithrombotic substance, a thrombolytic substance, or a mixture thereof, among other possibilities.

In accordance with one embodiment the present invention, the simultaneous radiation and therapeutic substance treatments are locally delivered to the treatment site by an intravascular catheter assembly. The catheter assembly includes a catheter body having a first end adapted to remain external to a patient's body, an opposite second end including a porous inflation region adapted to be positioned at the treatment site, a first lumen and a second lumen. The inflation region is adapted to inflate against a portion of a vascular wall, and to center the second lumen along a central axis of the vascular lumen at the treatment site. The inflation region is further adapted to deliver the therapeutic substance to the treatment site through pores in the inflation region. A radiation source is deliverable through the second lumen of the catheter body so as to provide the radiation treatment.

In accordance with another embodiment the present invention, a stent is implanted at the treatment site during the same surgical procedure as the simultaneous radiation and therapeutic substance treatments. One embodiment of an intravascular catheter assembly for performing such a procedure includes an inflation region including a substantially impermeable internal balloon, a permeable external balloon over the internal balloon, and a crimped stent wrapped over the external balloon. As above, the body of the catheter includes internal lumens, including lumens for inflating the internal and external balloons, and a central lumen through which the radiation source is delivered to the treatment site. Inflation of the inflation region results in deployment of the stent, centering of the central lumen in the vascular lumen, and delivery of the therapeutic substance through pores of the inflation region to the treatment site. The stent supports the vascular wall after completion of the procedure.

These and other features and aspects of the present invention will be better understood by consideration of the drawings and the following detailed description of the exemplary embodiments.

DETAILED DESCRIPTION OF THE EXEMPLARY EMBODIMENTS

Figure 1:
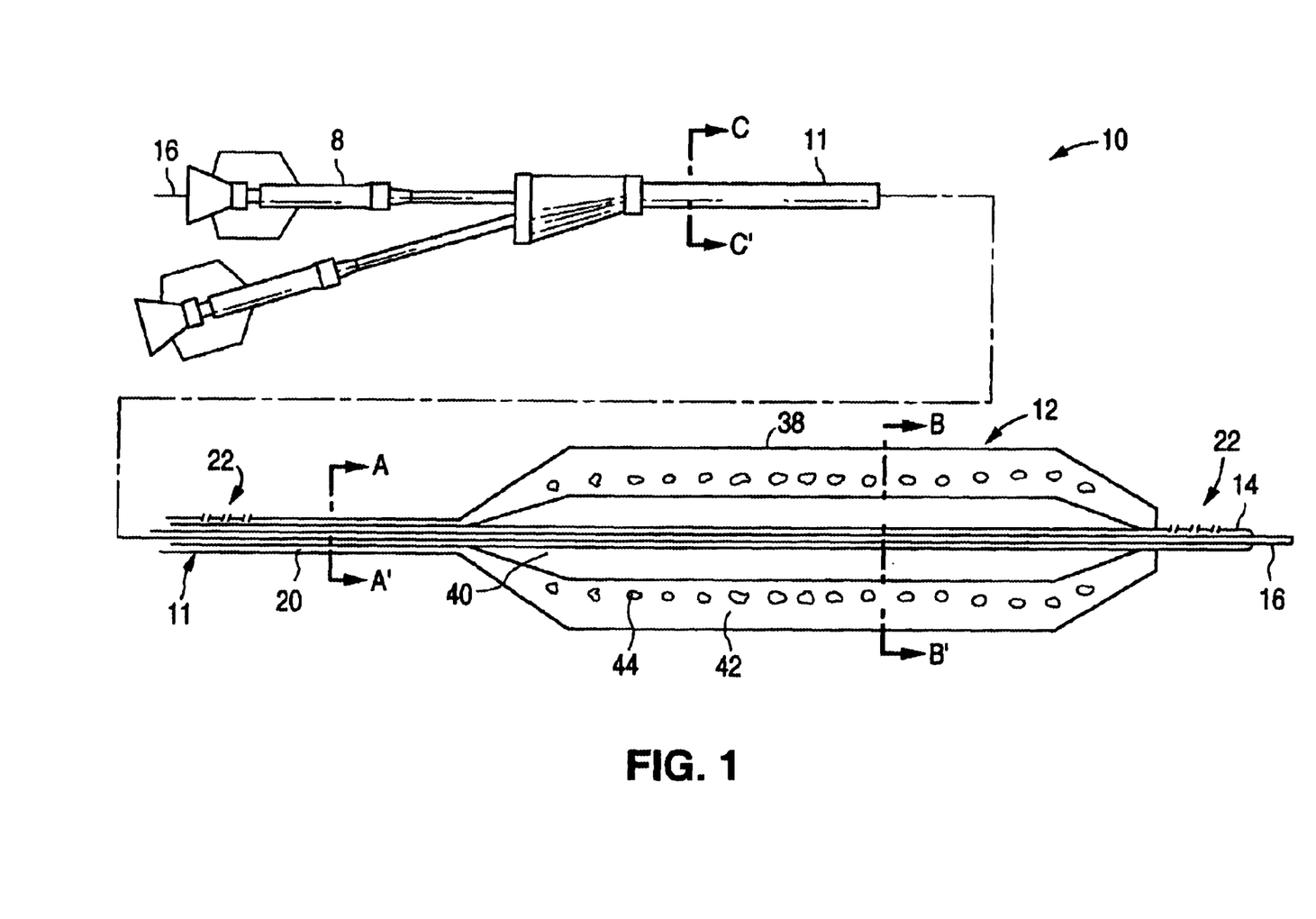
FIG. 1 is a side view and partial cross-sectional side view of an exemplary intravascular balloon catheter assembly.

FIG. 1 shows an intravascular balloon catheter assembly 10 in accordance with one embodiment of the present invention. Catheter assembly 10 may be used as part of a method within the present invention for reducing the likelihood of restenosis, or for other medicinal purposes, by delivering a local radiation treatment to an intravascular treatment site simultaneous with a local delivery of a therapeutic substance to the treatment site and adjacent tissue. In a typical application, the treatment site is in a coronary artery which had been the site of a previous PTCA procedure, and the therapeutic substance may be an antiplatelet, antithrombotic, or thrombolytic substance. Alternatively, catheter assembly 10 may be used in other body lumens as well, including peripheral arteries and veins.

In this exemplary embodiment, catheter 10 includes a proximal control portion 8 that is manipulated by the physician from outside of the patient's body, and a distal inflation region 12 that is inserted into the patient. Inflation region 12 is adapted for the local delivery of a therapeutic substance to the treatment site. A catheter body 11 (partially shown with broken lines) extends between control portion 8 and inflation region 12.

Figure 1A:
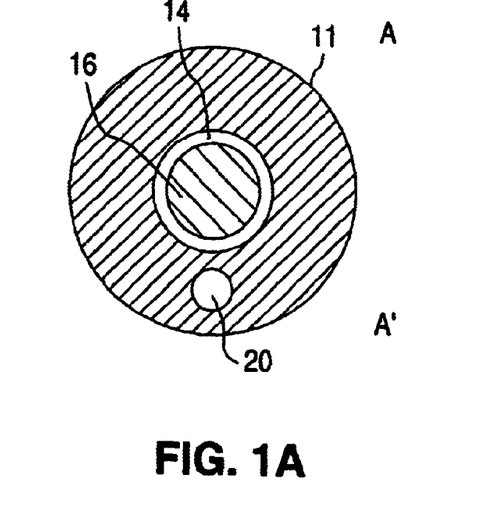
FIG. 1A is a cross-sectional view of the catheter of FIG. 1, taken in the direction of the arrows and along line A–A'.

As shown in FIG. 1A, this embodiment of catheter body 11 includes a central delivery lumen 14 and an inflation lumen 20 that extend through catheter body 11. The catheter assembly 10 can be delivered to a treatment site over a guide wire 16 that is threaded through delivery lumen 14. The guide wire 16 may include a core member, and a helical coil or other flexible body disposed about and fixed to the distal portion of the core member. A rounded plug of radiopaque material is typically provided at the distal tip of the coil. After inflation region 12 is in position at the treatment site and inflated against the vessel wall, guidewire 16 is removed, and a radiation source is passed through delivery lumen 14 to the treatment site.

Catheter assembly 10 can be formed from conventional materials of construction. The material forming catheter body 11 can be any metal or polymer with ductile properties which would be acceptable for the needs of intravascular devices. Specifically, the material chosen for the catheter body should have sufficient flexibility to easily advance and navigate through tortuous anatomy.

Inflation region 12 is adapted to inflate against a portion of a vascular wall defining the vascular lumen into which the catheter assembly is inserted (i.e., the treatment site), and to center the associated portion of delivery lumen 14 along a central axis of the vascular lumen at the treatment site. The inflation region 12 can be constructed of a single multi-lobed balloon, or of multiple individual balloons, wherein at least some portion of the balloon structure is porous so that the solution containing the therapeutic substance(s) can pass through the pores to the treatment site. Perfusion holes 22 may be provided in catheter body 11 to allow blood to continue flow through delivery lumen 14 while inflation region 12 is inflated.

For example, in FIG. 1, inflation region 12 includes three balloon lobes 38, 40, 42. Inflation region 12, including lobes 38, 40, 42, may be inflated by delivering a solution from control portion 8 through inflation lumen 20 to inflation region 12. When sufficiently inflated, lobes 38, 40, 42 will be positioned against a portion of the vascular wall, will center delivery lumen 14 in the vascular lumen at the treatment site, and will locally deliver the solution of the therapeutic substance. Alternatively, inflation region 12 may include more than three balloon lobes.

Pores 44 may be incorporated in inflation region 12 by, for example, laser drilling or track etching. For optimal distribution of the therapeutic substance, pores 44 may be distributed at regular intervals over the length of lobes 38, 40, 42. Pores 44 may be, for example 0.2 to 0.5 microns in diameter. Pores larger in diameter (e.g., 25 microns to 200 microns) may be used, but may pose a risk of injury to the patient due to jetting effects when the therapeutic substance exits the pores at a high velocity. Balloon lobes 38, 40, 42 may be made from, for example, polyethylene terephthalate (PET) or nylon, among other possibilities.

Upon inflation of inflation region 12 using, for example, an Indoflator® syringe at control portion 8 that maintains a constant delivery pressure, the solution containing the therapeutic substance will pass through pores 44 and be transported radially outward toward the treatment site. The Indoflator® syringe could deliver, for example, between 20 and 30 mL of an antiplatelet, antithrombotic, or thrombolytic substance, or mixture thereof at a constant pressure of three atmospheres.

Alternatively, inflation region 12 may include a spiral balloon wound about the central axis of delivery lumen 14. The spiral balloon wraps around the distal end of the catheter such that the spiral balloon is structurally nearly equivalent to a three-lobed balloon. A single lumen is used to inflate the spiral balloon. The spiral balloon is somewhat easier to manufacture than, for example, a multi-lobed balloon having three lobes. However, the spiral balloon is not quite as effective at centering itself within the target vessel as is a multi-lobed balloon.

Figure 2:
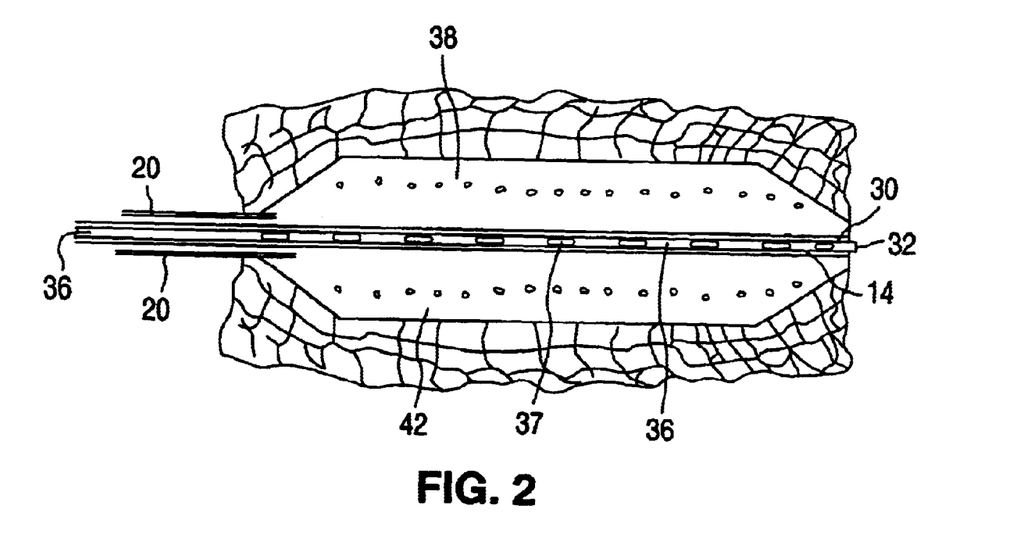
FIG. 2 is a cross-sectional view of the catheter assembly of FIG. 1 with a radiation source wire loaded in an internal lumen.

As mentioned above, delivery lumen 14 is adapted to allow the introduction of a radiation source to the treatment site. The guide wire 16 occupies the delivery lumen 14 while the catheter is delivered to the treatment site. Referring now to FIG. 2, once the catheter is in place and inflation region 12 is inflated and secure against the wall of the vascular lumen, the guide wire 16 is removed, and an internal lumen 30 is inserted into the delivery lumen 14. The internal lumen may be inserted into the catheter by using a support mandrel removably inserted into the internal lumen 30, and pushing it distally into the delivery lumen 14. The internal lumen 30 may be a blind (dead end) lumen sheath that is closed off at the distal end 32 to prevent entry of any body fluids such as blood into the internal lumen. The blind distal end 32 of the internal lumen 30 is placed at the inflation region 12 of the catheter. After the support mandrel is removed, a radiation source wire 36 is loaded into the blind internal lumen.

The radiation source wire 36 is inserted into the blind lumen for a period of time sufficient to deliver the required radiation dose to the body lumen. The distal end of the radiation source wire 36 contains a radiation dose in the form of radiation pellets 37. The radiation source wire alternatively can contain radioactive gas, liquid or paste, or have a radioactive source coated on its distal end. The radiation pellets 37 can be positioned at the appropriate location in the distal end of radiation source wire 36 to deliver the radiation dose. Inflation of the inflation region 12 to deliver the solution of the therapeutic substance centers the radiation source wire 36, and more specifically, the radiation pellets 37, within the artery so that uniform and equal amounts of radiation are applied to the vascular wall during treatment. The dosage of radiation delivered to the target site of the vascular lumen may be about 0.1 to 4.0 curies, e.g., about 1.0 to about 2.0 curies, for a time sufficient to deliver from about 500 to about 3000 rads. Meanwhile, the solution containing the therapeutic substance can be locally delivered to the treatment site through pores 44 in inflation region 12 before, during, and/or after the radiation therapy.

A method for preventing or mitigating restenosis within the present invention uses, in one interventional procedure, a local radiation therapy simultaneous with a local administration of a therapeutic substance. The therapeutic substance also may be delivered before, and/or after the local radiation therapy. Such a method may use catheter assembly 10 as follows.

Initially, inflation region 12 is positioned across the portion of the arterial passageway where a previous PTCA, atherectomy procedure, laser ablation, or some other procedure was performed. Alternatively, if some other condition is being treated, such as a tumor, the inflation region is positioned adjacent the target region. The steps of the method, as shown in FIG. 3, are discussed in conjunction with FIGS. 1, 1A, 2, and 4–9.

Figure 3:
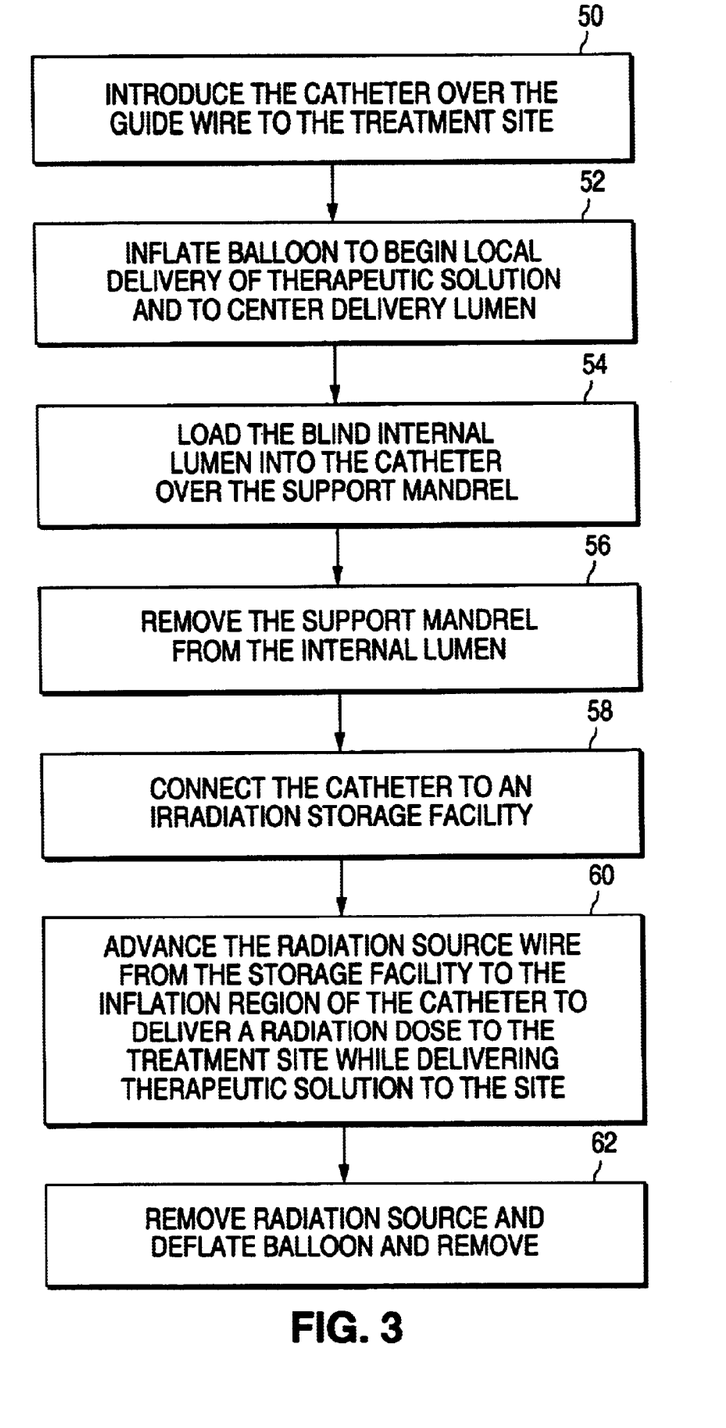
FIG. 3 is a flow chart describing the steps in a method of loading and centering the radiation source in a catheter in accordance with the present invention.
Figure 4:
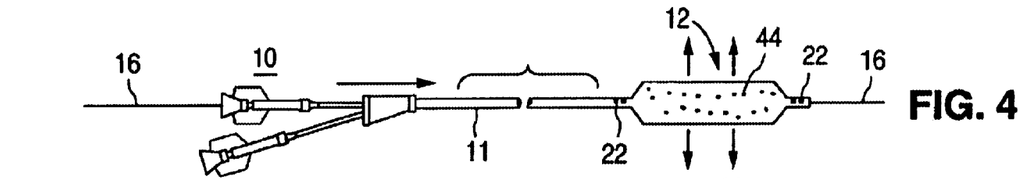
FIG. 4 is an elevational view of one embodiment of an intravascular catheter illustrating the first step of FIG. 3 in accordance with the present invention.

In step 50 of FIG. 3, the catheter assembly 10 is moved to the treatment site over a guide wire 16, as shown in FIG. 4, which may already be in place across the lesion as a result of a previous PTCA or other procedure.

Figure 5:
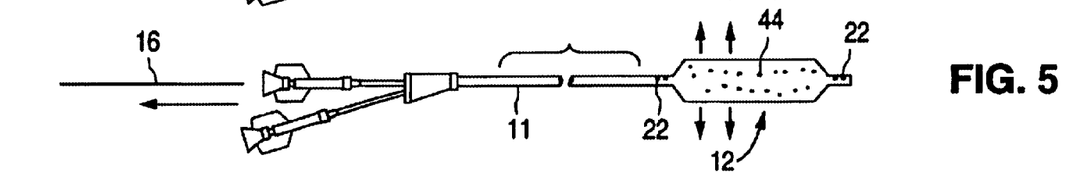
FIG. 5 is an elevational view of the catheter of FIG. 4, illustrating the second step of FIG. 3 in accordance with the present invention.

In step 52 of FIG. 3, balloon lobes 38, 40, 42 (see FIGS. 1 and 1A) are inflated. Such inflation puts the balloon lobes in contact with the vascular wall at the treatment site, centers the delivery lumen 14 the vascular lumen, and begins the local delivery of the solution of the therapeutic substance through the pores 44 in inflation region 12. As shown in FIG. 5, the guide wire 16 is then removed through the proximal end of the catheter assembly 10. The local delivery of the solution of the therapeutic substance is shown by radiating arrows in FIG. 4.

Figure 6:
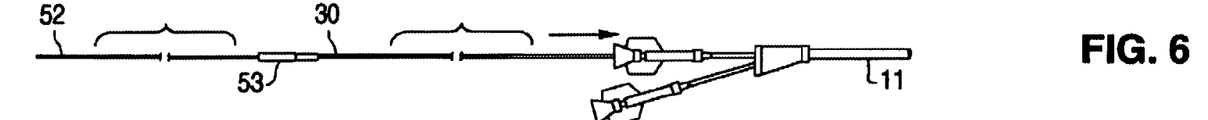
FIG. 6 is an elevational view of the catheter of FIG. 4 illustrating the third step of FIG. 3 in accordance with the present invention.

In step 54 of FIG. 3, once the inflation region 12 is expanded, the blind internal lumen 30 is loaded into delivery lumen of the catheter assembly over the support mandrel. As shown in FIG. 6, the support mandrel 52 supports blind internal lumen 30 during loading into the delivery lumen 14 (FIG. 1A). The support mandrel 52 is rigid enough to prevent the blind internal lumen 30 from collapsing on itself during loading, and flexible enough to allow for external loading while the catheter is situated in the patient's vasculature. The internal lumen 30 is loaded so that the blind distal end 32 is adjacent to the distal end of the inflation region 12. The proximal end of the internal lumen includes a Luer fitting 53 to provide access for the radiation source wire 36 into the catheter assembly through delivery lumen 14.

Figure 7:
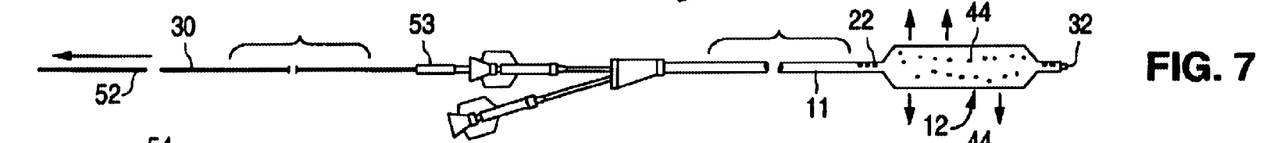
FIG. 7 is an elevational view of the catheter of FIG. 4 illustrating the fourth step of FIG. 3 in accordance with the present invention.

In step 56 of FIG. 3, the support mandrel 52 is removed from delivery lumen 14 through the proximal end of the catheter assembly 10, as shown in FIGS. 1A and 7.

Figure 8:
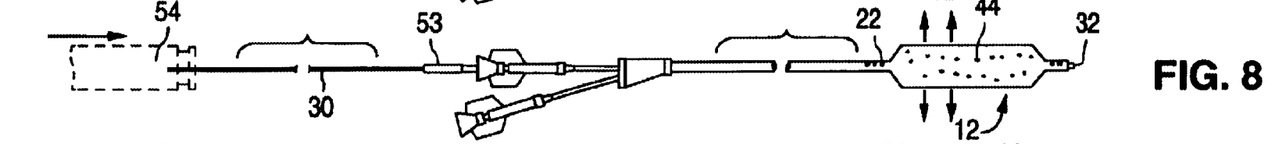
FIG. 8 is an elevational view of the catheter of FIG. 4 illustrating the fifth step of FIG. 3 in accordance with the present invention.

In step 58 of FIG. 3, the catheter is connected to an irradiation storage facility that loads the radiation source wire into the blind internal lumen 30. As shown in FIG. 8, the radiation storage facility 54 is connected to blind internal lumen 30 and the physician activates the facility to advance and load a predetermined length of radiation source wire into the catheter assembly. The radiation source wire 36 from the storage facility 54 is inserted into the proximal end of the blind internal lumen 30 through the Luer fitting 53.

Figure 9:
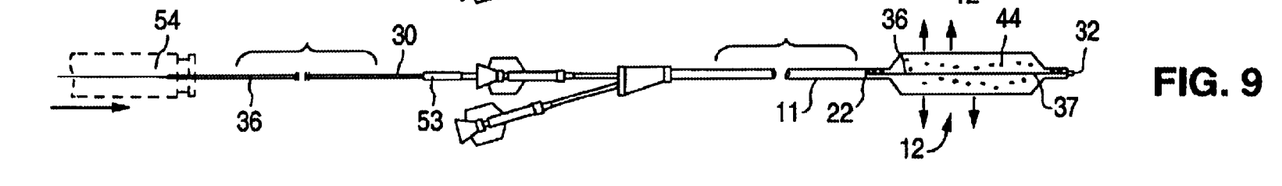
FIG. 9 is an elevational view of the catheter of FIG. 4 illustrating the fifth step of FIG. 3 in accordance with the present invention.

In step 60 of FIG. 3, as shown in FIG. 9, the radiation source wire 36 is loaded into delivery lumen 14 (FIG. 1A) until the distal end of the wire containing the radioactive source material reaches the blind distal end 32 of the internal lumen 30. The radiation source is positioned at the treatment site for a sufficient amount of time to allow a therapeutically significant amount of radiation to treat the area and prevent restenosis. The inflation region 12, when expanded, presses against the walls of the vascular lumen and centers the radiation source wire 36 and the radiation source 37 relative to the walls of the vascular lumen. Centering the radiation dose allows all portions of the artery to receive uniform and equal amounts of radiation therapy. Meanwhile, the solution of the therapeutic solution continues to be delivered through pores 44 in the inflation region 12 during the radiation treatment.

In step 62 of FIG. 3, after the radiation dose has been administered to the treatment area, the radiation source wire 36 can be removed from the catheter assembly and drawn back into the storage facility 54. Meanwhile, if desired, the solution of the therapeutic substance can continue to be delivered to the treatment site through pores 44 for a selected period of time. In addition, if desired, the inflation region 12 may be repositioned to locally deliver a dose of the therapeutic substance to a portion of the vascular lumen adjacent to the treatment site. Subsequently, delivery of the solution of therapeutic substance is ceased, and inflation region 12 is deflated. The catheter assembly 10 can then be withdrawn from the patient's vasculature.

For sustained local drug delivery after the radiation therapy, a drug delivery stent may be deployed to the treatment site following angioplasty and radiation treatment. As is known, a drug delivery stent may include one or more layers of a polymeric material within which one or more therapeutic substances are incorporated. The drug delivery stent also may have surface features, such as pore-like depots or a roughened surface, to enhance the loading of the polymeric material with drug and/or the retention of the polymeric material on the stent. This may be particularly desirable if the drug incorporated in the drug delivery stent helps the vessel heal faster, e.g., a nitric oxide donor or an endothelial cell promoter.

In accordance with another embodiment of the present invention, a stent is provided at the treatment site, in addition to the local radiation and drug therapy treatments. The stent is left inside the artery to provide support and keep the vessel open.

The physician's decision to perform angioplasty followed by radiation, as described earlier in the first embodiment of the method of the invention, with or without deploying a stent, is based on clinical factors. For example, where the patient has a long diseased section of artery, such as a length of 5 cm to 10 cm in a peripheral artery (e.g., the superficial femoral artery), the physician may choose angioplasty followed by radiation without stenting, since it is undesirable to line a long vessel with a metallic stent. On the other hand, a physician may choose to use angioplasty followed by radiation and stenting when the treatment site is a short de novo lesion (e.g., 5 mm to 15 mm in length).

Figure 10:
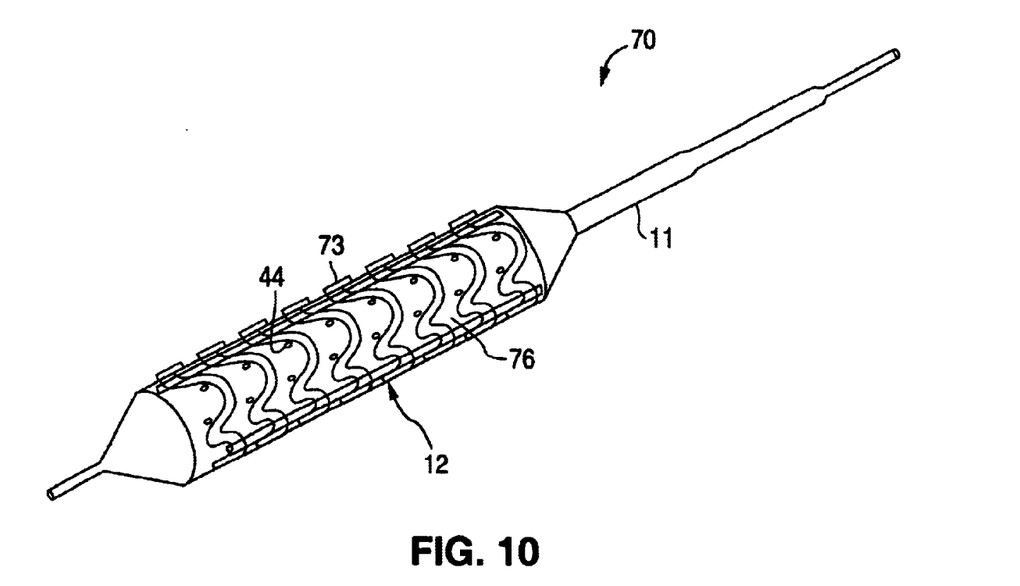
FIG. 10 is a side view of an exemplary intravascular device comprising a stent mounted on a distal end of a double balloon catheter assembly, wherein the outer balloon has pores.
Figure 11:
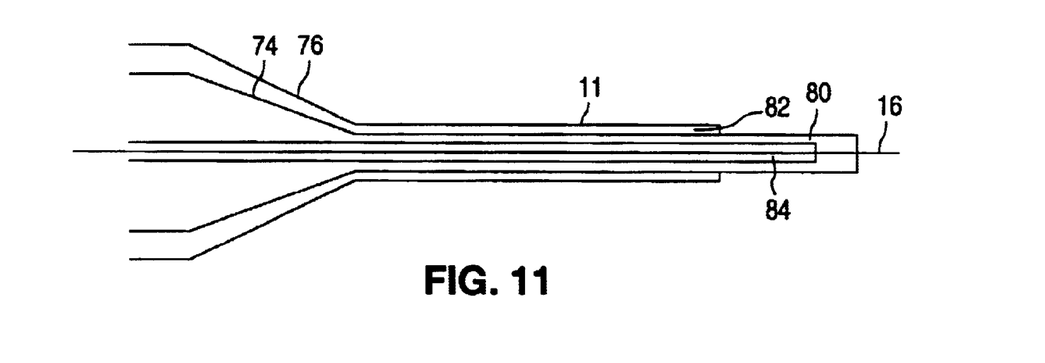
FIG. 11 is a partial cross-sectional view of the double balloon catheter assembly portion of the exemplary intravascular device of FIG. 10.
Figure 12:
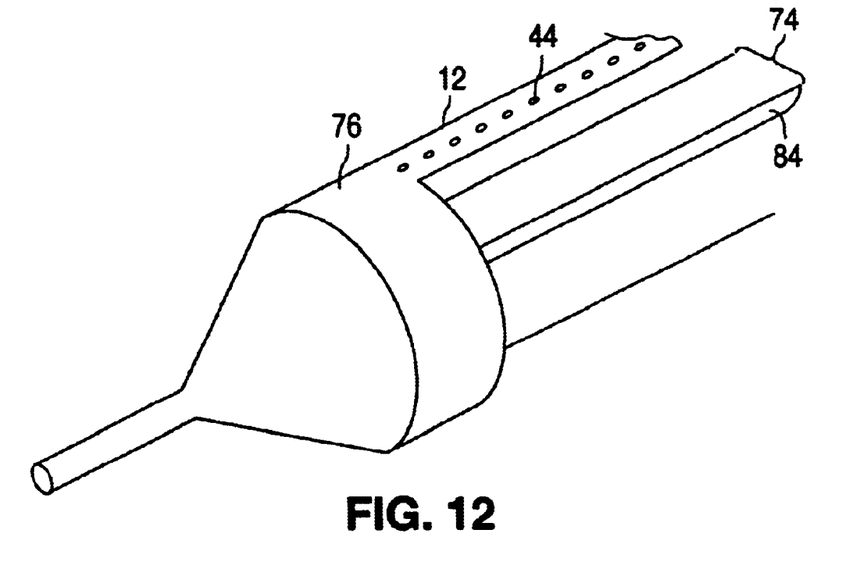
FIG. 12 is a partial cutaway view of the double balloon catheter assembly portion of the exemplary intravascular device of FIG. 10.

Portions of an exemplary intravascular catheter assembly 70 for locally providing simultaneous radiation and therapeutic substance treatments as well as a stent to an intravascular treatment site is shown schematically in FIGS. 10, 11, and 12. Intravascular catheter assembly 70 includes portions similar to catheter assembly 10 of FIG. 1, such as a body 11 (shown in part in FIGS. 10 and 11) and a distal inflation region 12. A stent 73 is wrapped around inflation region 12, and is deployed through inflation of inflation region 12 once inflation region 12 is at the treatment site.

Referring to FIGS. 10 and 12, intravascular catheter assembly 70 has a distal end including a substantially impermeable internal balloon 74. Internal balloon 74, being substantially impermeable, has no pores 44, and may be made from, for example, polyethylene terephthalate (PET). Intravascular catheter assembly 70 further includes a permeable external balloon 76. External balloon 76 is disposed around internal balloon 74, and is adapted to inflate against a portion of a vascular wall defining the vascular lumen. External balloon 76 is inflated by delivery of a solution containing at least one therapeutic substance. With inflation, external balloon 76 locally delivers the therapeutic solution to the treatment site. This may be achieved, for example, through pores 44 that are distributed over the length of external balloon 76, as shown in FIG. 11. Pores 44 may be, for example, 0.2 to 0.5 microns in diameter. External balloon 76 should have a burst pressure of about 75 p.s.i., and may be made from, for example, PET or nylon.

Stent 73 is positioned on external balloon 76 so as to be deployed when internal balloon 74 is inflated, as is commonly done to deploy such stents. In order to expand stent 73 such that the struts of stent 73 are anchored in the walls of the vasculature defining the vascular lumen, internal balloon 74 may need to be inflated to a pressure of about 12 atmospheres or so depending, of course, on the application.

To inflate internal and external balloons 74 and 76, while also providing a radiation source to the treatment site, body 11 includes at least three lumens, which are exemplified in FIG. 11 by first lumen 80, second lumen 82, and a central lumen 84 that has a similar function to delivery lumen 14 of intravascular catheter assembly 1 of FIGS. 1 and 1A.

In an exemplary method of use similar to that described above related to FIGS. 3–9, after inflation region 12 is positioned at the treatment site, internal balloon 74 is inflated using a saline solution or the like that is passed through first lumen 80. Inflation of internal balloon 74 causes stent 73 to be deployed such that the struts of stent 73 engage a portion of the vascular wall. External balloon 76, being disposed around internal balloon 74, expands and stretches, but is not "inflated" by the action of internal balloon 74. When inflated, internal balloon 74 centers third lumen 84 along a central axis of the vascular lumen. External balloon 76 is then inflated through second lumen 82 with a solution containing a therapeutic substance, using, for example, in Indoflator® syringe as described above. After external balloon 76 is fully inflated, the solution containing the therapeutic substance(s) begins to pass through pores 44 to the treatment site. Then, guidewire 16 is removed from third lumen 84, and a radiation source is provided to the treatment site through third lumen 84, as described above. After the simultaneous treatment with the locally delivered therapeutic substance and radiation, the radiation source is removed, inflation region 12 is deflated, and catheter assembly 70 is withdrawn from the patient. Meanwhile, stent 73 remains at the treatment site to support the vascular lumen.

In an alternative embodiment, stent 73 may also be coated with a therapeutic substance (typically in a polymer carrier), for sustained delivery of a therapeutic substance to the treatment site after the surgical procedure.

Figure 13A:
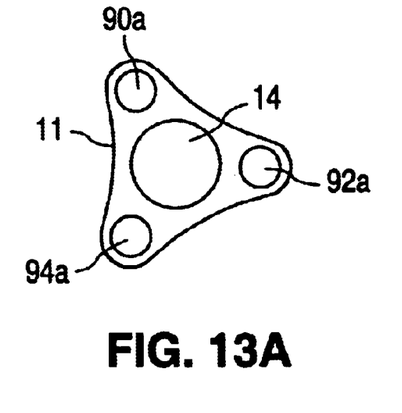
FIG. 13A is a cross-sectional view of an alternative embodiment of a catheter shaft for the catheter assembly of FIG. 1, taken in the direction of the arrows and along line B–B'.

As should be apparent from the above discussion, the present invention is not limited to particular catheter configurations. For example, the catheter body 11 may have several different designs in accordance with the invention. As illustrated in FIG. 13A, three independent, circular inflation/infusion lumens may be disposed within catheter body 11. Inflation/infusion lumens 90a, 92a, and 94a are used to inflate lobes 38, 40, and 42 of FIG. 1, respectively. Inflation/infusion lumens 90a, 92a, and 94a are so named because they are used to both inflate the lobes 38, 40, and 42 into contact with the treatment site, and to medicate a treatment site with a therapeutic substance (e.g., an antithrombotic, antiplatelet, or thrombolytic substance or a combination of these). Advantageously, each inflation/infusion lumen may transport a different therapeutic substance to and through a different lobe.

Figure 13B:
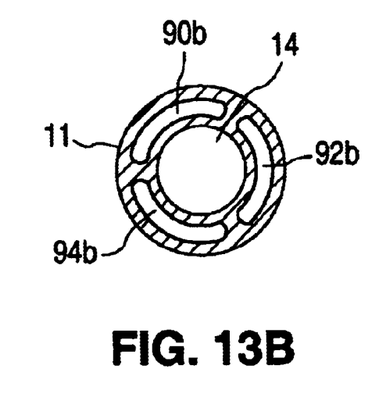
FIG. 13B is a cross-sectional view of another embodiment of a catheter shaft for the catheter assembly of FIG. 1, taken in the direction of the arrows and along line B–B'.

According to another embodiment of body 11, the three independent inflation/infusion lumens may be crescent-shaped in cross-sectional profile, rather than circular, as illustrated in FIG. 13B. Advantageously, crescent-shaped lumens 90b, 92b, and 94b permit catheter body 11 to have a lower cross-sectional profile, which in turn facilitates accessing more tortuous vasculature within the patient, in addition to providing the capability to transport different therapeutic substances simultaneously.

Figure 13C:
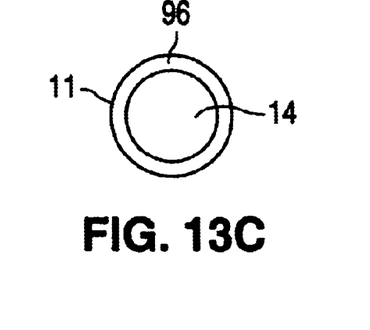
FIG. 13C is a cross-sectional view of another embodiment of a catheter shaft for the catheter assembly of FIG. 1, taken in the direction of the arrows and along line B–B'.

FIG. 13C illustrates still another embodiment of body 11, wherein a single, common inflation/infusion lumen 96 is used to inflate all of the lobes 38, 40, and 42 of FIG. 1 (which in this case are in fluid communication with each other) and to infuse the treatment site with a therapeutic substance. Of course, in this embodiment, only one therapeutic substance may be delivered at a time.

A wide variety of therapeutic substances may be locally delivered to the treatment site with the radiation treatment, in accordance with the invention. For example, an antiplatelet substance, an antithrombotic substance, a thrombolytic substance, or a combination thereof may be delivered. Antiplatelet substances prevent platelet activation and aggregation. Antiplatelet substances include aspirin, dipyridamole, triclopidine, clopidogrel, and GP IIb/IIIa inhibitors (described below).

The process of platelet adhesion to damaged endothelium is mediated through the glycoprotein (GP) IIb/IIIa receptor and may be blocked by agents that bind to the receptor. Such agents are termed GP IIb/IIIa inhibitors herein.

GP IIb/IIIa inhibitors such as abciximab, tirofiban, and eptifibatide may be used. While all three agents share a biologic target, they are different in other respects, including the physical binding site on the receptor (which regulates specificity), dissociation kinetics (governing affinity), stoichiometry for inhibition, clearance mechanisms, and plasma and biologic half-lives.

Antithrombotic substances prevent thrombin activity and generation. Antithrombotic substances include, for example, heparin and low molecular weight heparins, such as hirudin.

Thrombolytic substances dissolve clots by fibrinolysis. Thrombolytic substances include, for example, streptokinase, antistreplase, urokinase, tPA, and reteplase.

Advantageously, in practicing the invention, an antithrombotic effect is achieved without any increase in procedure time, since administration of therapeutic substances is performed simultaneously with administration of radiation therapy. Moreover, the invention also permits the local delivery of a drug to the target vessel which promotes reendothelialization. Vascular endothelial growth factor (VEGF), is an example of such a drug.

Radiation sensitizers may also be locally delivered to the treatment site. Such are chemical compounds that weaken cells, making the DNA of the cells more susceptible to lysing by radioactive agents. An example of such a compound is actinomycin D. The physician practicing one of the methods of the present invention may choose to administer a radiation sensitizer to the treatment site, (e.g., through external balloon 76, in one embodiment of an intravascular device) in order to increase the susceptibility of cells in the treatment site to the radiation therapy subsequently administered. However, in selecting the radiation sensitizer, the physician must consider the interaction of the radiation sensitizer with the therapeutic substance that is administered in conjunction with the radiation therapy (e.g., antiplatelet, antithrombotic, or thrombolytic substances or mixtures thereof), to ensure the effectiveness of the therapeutic substance(s) is not impaired. The physician must also consider the radiation dose based on the effectiveness of the radiation sensitizer.

Practitioners will appreciate that the embodiments described above are exemplary only. Other ways of locally delivering a therapeutic substance and a therapeutic substance to a treatment site may be apparent in view of the disclosure herein. The claims below set forth our invention.

What is claimed is:

1. An intravascular catheter assembly comprising:

a body including
      a first end adapted to remain external to a patient's body;
      an opposite second end including a porous inflation region adapted to be positioned at a treatment site within a vascular lumen of said patient's body;
      one or more first lumens that deliver a solution that inflates said inflation region and passes through said pores to said treatment site; and
      a second lumen, wherein said porous inflation region is adapted to center said second lumen in said vascular lumen at said treatment site upon the inflation of said porous inflation region; and
   a radiation source adapted to be delivered through said second lumen from said first end to said second end of said body to provide a radiation treatment at said treatment site.

2. The intravascular catheter assembly of claim 1, wherein said second lumen is adapted to prevent exposure of said radiation source to bodily fluids.

3. The intravascular catheter assembly of claim 1, wherein said inflation region comprises at least three lobes, said lobes adapted to contact said vascular lumen when said inflation region is inflated.

4. The intravascular catheter assembly of claim 3, wherein each of said lobes is in fluid communication with at least one of said first lumens.

5. The intravascular catheter assembly of claim 3, wherein said body includes a single first lumen for delivery of the solution to said at least three lobes.

6. The intravascular catheter assembly of claim 1, wherein said inflation region comprises a spiral balloon wound about the central axis of said second lumen.

7. An intravascular device comprising:

a catheter body including
      a first end adapted to remain external to a patient's body, and
      an opposite second end including an inflation region, said inflation region including a substantially impermeable internal balloon, a permeable external balloon disposed over said internal balloon, and a first lumen, a second lumen, and a third lumen disposed within said catheter body,
      wherein said internal balloon is adapted to inflate by delivery of a solution from said first end through said first lumen and to center said third lumen along a central axis of said vascular lumen, and said external balloon is adapted to inflate by delivery of a second solution from said first end through said second lumen and to deliver said second solution to a treatment site through said external balloon;
   a radiation source adapted to be delivered through said third lumen from said first end to said second end to provide a radiation treatment at said treatment site; and
   a stent positioned over said external balloon of the inflation region.

8. The intravascular device of claim 7, wherein said third lumen is adapted to prevent exposure of the radiation source to bodily fluids.

9. An intravascular catheter assembly, comprising:

a body including
- a first end adapted to remain external to a patient's body;
- an opposite second end adapted to be positioned at a treatment site within a vascular lumen of said patient's body, said second end having a first elongated balloon, a second elongated balloon and a third elongated balloon, wherein at least one of said balloons is porous; and
- one or more first lumens disposed along a length of said body that deliver a solution that inflates said at least one porous balloon and passes through the pores of said balloon to said treatment site, and
- a second lumen disposed along a length of said body, wherein said first, second and third balloons are positioned along a length of said second lumen and are radially spaced from each other such that said balloons center said second lumen in said vascular lumen at said treatment site upon the inflation of said first, second and third balloons; and
- a radiation source adapted to be delivered through said second lumen from said first end to said second end of said body to provide a radiation treatment at said treatment site.

10. The intravascular catheter assembly of claim 9, wherein said second lumen is adapted to prevent exposure of the radiation source to bodily fluids.

* * * * *

UNITED STATES PATENT AND TRADEMARK OFFICE
CERTIFICATE OF CORRECTION

PATENT NO. : 6,645,135 B1
DATED : November 11, 2003
INVENTOR(S) : Vinayak D. Bhat It is certified that error appears in the above-identified patent and that said Letters Patent is hereby corrected as shown below:

<u>Column 8,</u>
Line 21, change "catheter assembly 1" to -- catheter assembly 10 --.

<u>Column 9,</u>
Line 37, change "beparin" to -- heparin --.

Signed and Sealed this

Second Day of March, 2004

JON W. DUDAS
*Acting Director of the United States Patent and Trademark Office*